United States Patent
De La Mettrie et al.

(10) Patent No.: US 7,740,663 B2
(45) Date of Patent: Jun. 22, 2010

(54) ANHYDROUS COMPOSITIONS IN PASTE FORM FOR BLEACHING KERATIN FIBERS

(75) Inventors: Roland De La Mettrie, le Vesinet (FR); Benoit Boche, la Garenne Colombes (FR)

(73) Assignee: L'Oreal S.A., Paris (FR)

(*) Notice: Subject to any disclaimer, the term of this patent is extended or adjusted under 35 U.S.C. 154(b) by 174 days.

(21) Appl. No.: 12/215,390

(22) Filed: Jun. 27, 2008

(65) Prior Publication Data

US 2009/0095315 A1    Apr. 16, 2009

Related U.S. Application Data

(60) Provisional application No. 60/929,797, filed on Jul. 12, 2007.

(30) Foreign Application Priority Data

Jun. 29, 2007    (FR)    .................................. 07 56184

(51) Int. Cl.
*D06L 3/02* (2006.01)

(52) U.S. Cl. .............................................. 8/107; 8/111

(58) Field of Classification Search .................... 8/107, 8/111
See application file for complete search history.

(56) References Cited

U.S. PATENT DOCUMENTS

| | | | |
|---|---|---|---|
| 4,170,637 A | 10/1979 | Pum | |
| 4,826,681 A | 5/1989 | Jacquet et al. | |
| 5,674,436 A | 10/1997 | Breitenbach et al. | |
| 5,753,770 A | 5/1998 | Breitenbach et al. | |
| 5,945,032 A * | 8/1999 | Breitenbach et al. | ... 252/186.29 |
| 7,399,319 B2 | 7/2008 | Plos | |
| 2004/0181883 A1 | 9/2004 | Legrand et al. | |

FOREIGN PATENT DOCUMENTS

| | | |
|---|---|---|
| DE | 43 44 131 | 6/1995 |
| DE | 195 45 380 | 6/1997 |
| EP | 0 193 471 | 9/1986 |
| EP | 0 714 919 | 6/1996 |
| EP | 0 832 846 | 4/1998 |
| EP | 1 430 875 | 6/2004 |
| EP | 1 747 774 | 1/2007 |
| WO | WO 93/14024 | 7/1993 |

OTHER PUBLICATIONS

English language Abstract for DE 195 45 380, dated Jun. 12, 1997.
French Search Report for FR 07/56184, dated Feb. 13, 2008.
* cited by examiner

*Primary Examiner*—Eisa B Elhilo
(74) *Attorney, Agent, or Firm*—Finnegan, Henderson, Farabow, Garrett & Dunner, L.L.P.

(57) ABSTRACT

The present disclosure relates to an anhydrous composition in paste form for bleaching keratin fibers, comprising at least one peroxygenated salt, at least one alkaline agent, and at least one complex of hydrogen peroxide and of at least one polymer comprising, as a monomer, at least one vinyl heterocyclic monomer. This disclosure also related to the use and preparation of said composition.

34 Claims, No Drawings

ANHYDROUS COMPOSITIONS IN PASTE FORM FOR BLEACHING KERATIN FIBERS

This application claims benefit of U.S. Provisional Application No. 60/929,797, filed Jul. 12, 2007, the contents of which are incorporated herein by reference. This application also claims benefit of priority under 35 U.S.C. §119 to French Patent Application No. FR 0756184, filed Jun. 29, 2007, the contents of which are also incorporated herein by reference.

The present disclosure relates to an anhydrous composition in paste form for bleaching keratin fibers, for example human keratin fibers such as the hair, comprising at least one peroxygenated salt, at least one alkaline agent, and at least one complex of hydrogen peroxide and of at least one polymer comprising, as a monomer, at least one vinyl heterocyclic monomer.

The disclosure also relates to the process for bleaching human keratin fibers using such a composition.

Human keratin fibers, such as the hair, can be bleached by oxidizing the "melanin" pigment, resulting in the dissolution and partial or total removal of this pigment.

To bleach the hair, use may be made of bleaching powders containing a peroxygenated reagent such as ammonium or alkali metal persulfates, perborates and percarbonates, which are combined at the time of use with an aqueous hydrogen peroxide composition.

Since peroxygenated salts and hydrogen peroxide are relatively stable in acidic medium, it is often necessary to activate them at basic pH to obtain an adequate formation of oxygen. It is thus common practice to add to bleaching powders alkaline compounds such as urea, alkali metal or alkaline-earth metal silicates and phosphates, for example alkali metal metasilicates or ammonia precursors such as ammonium salts.

Bleaching powders have a tendency to form dust during their handling, transportation and storage, and since the products of which they are composed (alkali metal silicates and persulfates) are corrosive and irritant to the eyes, the respiratory pathways and mucous membranes, pastes have recently been developed, for example comprising the pulverulent bleaching agents in a thickened organic inert liquid support. Such compositions are described, for example, in patent applications DE-3814 356 A1, DE-197 23 538 C1 and U.S. Pat. No. 4,170,637.

Bleaching powders and pastes are conventionally mixed, just before use, with an aqueous hydrogen peroxide solution.

Thus, U.S. patent application publication no. 2006/0254001 describes an oxidizing composition that may be used, for example, for bleaching, which is obtained by mixing:
  a first solid or pasty anhydrous composition (A), containing an agglomerate of alkaline agent and of chelating agent, and
  a second aqueous or aqueous-alcoholic composition (B), one and/or the other of the two compositions (A) and (B) comprising hydrogen peroxide in solution or in the form of a solid adduct of hydrogen peroxide with an organic or mineral compound.

In at least one embodiment, only the liquid composition (B) contains hydrogen peroxide.

Moreover, patent application publication WO 93/14024 describes hair bleaching compositions in powder form, containing, inter alia, ammonium or potassium persulfate and sodium carbonate, to which are added at the time of use 5% by weight of a complex of polyvinylpyrrolidone and hydrogen peroxide, and also 20 volumes of an aqueous hydrogen peroxide-based developing cream.

Persalt-based pulverulent compositions nevertheless pose problems of instability, on the one hand, and of harmfulness, on the other hand, associated with the volatility of the products.

Moreover, the use of the aqueous hydrogen peroxide compositions may also pose a problem. Specifically, these compositions are relatively irritating to the skin, and above all to the eyes and mucous membranes, with which all contact should be avoided.

These problems are all the more prevalent the higher the hydrogen peroxide concentration in the aqueous composition.

There is thus a need to reduce the amounts or the concentrations of hydrogen peroxide in solutions used, or even to dispense entirely with the use of hydrogen peroxide solutions.

Applicants have now discovered that the use, in anhydrous bleaching pastes, of a complex as described below may allow these problems to be overcome.

One aspect of the present disclosure is thus an anhydrous composition in powder form for bleaching keratin fibers, comprising at least one peroxygenated salt, at least one alkaline agent, and at least one complex of hydrogen peroxide and of at least one polymer comprising, as a monomer, at least one vinyl heterocyclic monomer.

The bleaching composition according to the present disclosure has the advantage of being able to be used as a mixture with an aqueous composition optionally comprising hydrogen peroxide.

When it is used without hydrogen peroxide, the composition according to the disclosure is diluted at the time of use with an aqueous composition not comprising hydrogen peroxide, for example, but not limited to, a non-oxidizing aqueous composition. In at least one embodiment, this aqueous composition may be water, which may make it possible to simplify the procedure and the conditioning of the bleaching composition, and to reduce the costs.

When it is used with an aqueous hydrogen peroxide composition, such as, but not limited to, a solution of hydrogen peroxide in water, the composition according to the disclosure may have the advantage of making it possible to reduce the concentration of the hydrogen peroxide solution, while still obtaining very high quality lightening.

However, if a solution of a normal or conventional concentration of hydrogen peroxide is used, the composition according to the disclosure may have the additional advantage of allowing the production of lightening that is superior to that which would be obtained with a standard paste not comprising any complex of at least one polymer and of hydrogen peroxide, this being achieved without additional degradation of the keratin fiber. On the other hand, if the amount of persulfates in a standard bleaching paste is increased, or if the concentration of the hydrogen peroxide solution is increased, there is a risk of degrading the keratin fibers during the bleaching treatment.

Another aspect of the present disclosure is the use of the anhydrous composition in the form of a paste according to the disclosure, for the preparation of a ready-to-use bleaching composition.

For the purposes of the present disclosure, the term "ready-to-use composition" means the composition intended to be applied to keratin fibers in its native form, i.e. it results from the extemporaneous mixing of the anhydrous composition in paste form and of the aqueous composition optionally comprising hydrogen peroxide.

The disclosure is also directed towards a process for bleaching human keratin fibers, such as the hair, using the ready-to-use bleaching composition according to the disclosure.

Other characteristics, aspects, and advantages of the disclosure will emerge even more clearly on reading the description and the examples that follow.

For the purposes of the disclosure, the term "anhydrous" means a composition whose water content is less than 1% by weight, for example, but not limited to, less than 0.5% by weight, relative to the total weight of the composition.

For the purposes of the disclosure, the term "paste" means a composition having a consistency that is intermediate between a solid and a liquid, for example, but not limited to, having a viscosity of greater than 5 poises, such as greater than 10 poises at 25° C., and at a shear rate of 1 s$^{-1}$. This viscosity may be measured using a rheometer or a cone-plate viscometer.

The composition according to the disclosure comprises at least one peroxygenated salt, which may be, chosen from, but is not limited to, ammonium or alkali metal persulfates, perborates and percarbonates and also magnesium peroxide, and mixtures of these compounds.

In at least one embodiment, persulfates are used, for example, sodium and potassium persulfates.

In the composition according to the disclosure, the at least one peroxygenated salt may be present in a concentration ranging from 10% to 70% by weight, for example, but not limited to, from 20% to 60% by weight, relative to the total weight of the composition.

The composition according to the disclosure comprises at least one alkaline agent, which may be chosen from, but are not limited to, aqueous ammonia and alkali metal or alkaline-earth metal silicates, metasilicates, phosphates, hydrogen phosphates, carbonates and hydrogen carbonates, such as alkali metal metasilicates.

The at least one alkaline agent may be present in the composition according to the disclosure in a concentration ranging from 0.01% to 40% by weight, for example, but not limited to, from 0.1% to 30% by weight, relative to the total weight of the composition.

In at least one embodiment, the at least one alkaline agent may be present in an aqueous composition to be mixed at the time of use with the composition according to the disclosure.

According to another embodiment, the composition according to the disclosure further comprises at least one ammonium salt, non-limiting examples of which include ammonium chloride, ammonium sulfate, ammonium phosphate or ammonium nitrate. The at least one ammonium salt may be present, for example, in the composition according to the disclosure in a concentration ranging from 0.01% to 40% by weight, for example, but not limited to, from 0.1% to 30% by weight, relative to the total weight of the composition.

The composition according to the disclosure also comprises at least one complex of hydrogen peroxide and of at least one polymer comprising, as a monomer, at least one vinyl heterocyclic monomer.

In at least one aspect of the disclosure, the at least one vinyl heterocyclic monomer is chosen from monomers comprising a 4- to 6-membered heterocycle, optionally fused to a benzene ring, and comprises from 1 to 4 identical or different endocyclic heteroatoms; the number of endocyclic heteroatoms being less than the number of ring members in the heterocycle. In at least one embodiment, the number of endocyclic heteroatoms is 1 or 2.

In a further aspect of the disclosure, the heteroatom or heteroatoms are chosen from sulfur, oxygen and nitrogen, for example from nitrogen and oxygen. In accordance with another embodiment of the disclosure, the at least one vinyl heterocyclic monomer comprises at least one endocyclic nitrogen atom.

The at least one vinyl heterocycle monomer may optionally be substituted with at least one $C_1$-$C_4$, for example $C_1$-$C_2$, alkyl group.

In at least one embodiment, the at least one vinyl heterocyclic monomer is chosen from N-vinyl monomers.

Among the monomers that may be envisaged, non-limiting mention may be made of the following optionally substituted monomers: N-vinylpyrrolidone, vinylcaprolactam, N-vinylpiperidone, N-vinyl-3-morpholine, N-vinyl-4-oxazolinone, 2-vinylpyridine, 4-vinylpyridine, 2-vinylquinoline, 1-vinylimidazole and 1-vinylcarbazole.

In accordance with at least one embodiment of the disclosure, the polymer is a homopolymer.

However, use of a copolymer is not excluded. In such a case, the at least one comonomer is chosen from vinyl acetate, (meth)acrylic acids, (meth)acrylamides, and substituted or unsubstituted $C_1$-$C_4$ alkyl esters of (meth)acrylic acid.

The at least one polymer included in the at least one complex may be water-soluble or water-insoluble. In at least one aspect of the disclosure, it is water-soluble. It may have variable average molecular weights, for example, but not limited to, in a range from $10^3$ to $3\times10^6$ g/mol, such as from $10^3$ to $2\times10^6$ g/mol. It is also possible to use mixtures of such polymers.

Non-limiting examples of complexes of hydrogen peroxide with polymers of this type are described in patents EP 832 846, EP 714 919, DE 4344131 and DE 195 45 380.

In at least one aspect of the disclosure, the at least one complex comprises from 10% to 30% by weight, for example from 13% to 25% by weight and from 18% to 22% by weight of hydrogen peroxide, relative to the total weight of the complex.

According to a variant of the disclosure, in the at least one complex, the mole ratio between the at least one vinyl heterocyclic monomer and the hydrogen peroxide ranges from 0.5 to 2, for example from 0.5 to 1.

The at least one complex is, in at least one embodiment, in the form of a substantially anhydrous powder, i.e. a powder comprising less than 5% by weight of water. It may be prepared in a known manner, for example, but not limited to, those described in U.S. Pat. No. 5,008,106 or U.S. Pat. No. 5,077,047.

Non-limiting examples of complexes of this type that may be mentioned include products such as PEROXYDONE® K-30, PEROXYDONE® K-90 and PEROXYDONE® XL-10, and also complexes formed with hydrogen peroxide and one of the following polymers: PLASDONE® K-17, PLASDONE® K-25, PLASDONE® K-29/32, PLASDONE® K-90, POLYPLPASDONE® INF-10, POLYPLPASDONE® XL-10, Polyplasdone XL, PLASDONE® S-630, STYLEZE® 2000 Terpolymer, and the GANEZ® series of copolymers, sold by the company ISP.

At least one aspect of the anhydrous composition according to the disclosure, comprises from 0.1% to 50% by weight, for example from 0.1% to 30% by weight and from 1% to 25% by weight of the at least one complex of hydrogen peroxide and of at least one polymer comprising, as monomer, at least one vinyl heterocyclic monomer, relative to the total weight of the composition.

Another aspect of the composition according to the disclosure, comprises at least one organic inert liquid, which may be, for example, chosen from, but is not limited to, the group formed by the polydecenes of formula $C_{10n}H_{[(20n)+2]}$ wherein n is an integer ranging from 3 to 9, esters of fatty alcohols or of fatty acids, esters or diesters of sugars and of $C_{12}$-$C_{24}$ fatty acids, cyclic ethers or cyclic esters, silicone oils, mineral oils and plant oils, and mixtures thereof.

For the purposes of the present disclosure, the term "liquid" means a compound that is capable of flowing at room temperature, for example from 15° C. to 40° C., and at atmospheric pressure, under the action of its own weight.

The term "inert" means that the liquid does not react, at least under the storage conditions, with the ingredients of the composition.

Non-limiting examples of the at least one inert liquid that may be mentioned include the polydecenes of formula $C_{10n}H_{[(20n)+2]}$ wherein n is an integer ranging from 3 to 9 and for example from 3 to 7, esters, for example esters of fatty alcohols or of fatty acids, sugar esters or diesters of $C_{12}$-$C_{24}$ fatty acids, cyclic esters, cyclic ethers, silicone oils, mineral oils, plant oils and animal oils, and mixtures thereof.

The compounds of formula $C_{10n}H_{[(20n)+2]}$ wherein n is an integer ranging from 3 to 9 correspond to the name "polydecene" of the CTFA dictionary, 7th edition, 1997 of the Cosmetic, Toiletry and Fragrance Association, USA, and also to the same INCI name in the USA and in Europe. These are poly-1-decene hydrogenation products.

In at least one embodiment, these compounds are chosen wherein n ranges from 3 to 7.

Non-limiting examples that may be mentioned include the products sold under the name SILKFLO® 366 NF Polydecene by the company Amoco Chemical, and those sold under the name NEXBASENexbase® 2002 FG, 2004 FG, 2006 FG and 2008 FG by the company Fortum.

With regard to the esters, non-limiting examples that may be mentioned include:
  esters of saturated, linear or branched $C_3$-$C_6$ lower monoalcohols with monofunctional $C_{12}$-$C_{24}$ fatty acids, these fatty acids optionally being linear or branched, saturated or unsaturated and chosen, for example, from oleates, laurates, palmitates, myristates, behenates, cocoates, stearates, linoleates, linolenates, caprates and arachidonates, or mixtures thereof, such as oleo-palmitates, oleo-stearates and palmito-stearates. In at least one embodiment, the ester is chosen from isopropyl palmitate, isopropyl myristate, octyldodecyl stearate, and isononyl isononanoate;
  esters of linear or branched $C_3$-$C_8$ monoalcohols with difunctional $C_8$-$C_{24}$ fatty acids, these fatty acids optionally being linear or branched, and saturated or unsaturated, for instance the isopropyl diester of sebacic acid, also known as diisopropyl sebacate;
  esters of linear or branched $C_3$-$C_8$ monoalcohols with difunctional $C_2$-$C_8$ fatty acids, these fatty acids optionally being linear or branched, and saturated or unsaturated, for instance dioctyl adipate and dicaprylyl maleate; and
  the ester of a trifunctional acid, for instance triethyl citrate.

With regard to the sugar esters and diesters of $C_{12}$-$C_{24}$ fatty acids, the term "sugar" means compounds comprising several alcohol functions, with or without an aldehyde or ketone function, and which comprise at least 4 carbon atoms. These sugars may be monosaccharides, oligosaccharides or polysaccharides.

As sugars that may be used according to the disclosure, non-limiting examples that may be mentioned include sucrose (or saccharose), glucose, galactose, ribose, fucose, maltose, fructose, mannose, arabinose, xylose and lactose, and derivatives thereof, for example alkyl derivatives such as methyl derivatives, for instance methylglucose.

Non-limiting examples of the sugar esters of fatty acids that may be used according to the disclosure include those from the group comprising esters or mixtures of esters of sugars described above and of linear or branched, saturated or unsaturated $C_{12}$-$C_{24}$ fatty acids.

The esters may be chosen from mono-, di-, tri-, tetraesters and polyesters, and mixtures thereof.

These esters may be chosen from, for example, but not limited to, oleates, laurates, palmitates, myristates, behenates, cocoates, stearates, linoleates, linolenates, caprates and arachidonates, or mixtures thereof such as oleo-palmitate, oleo-stearate and palmito-stearate mixed esters.

In at least one embodiment, sucrose, glucose or methylglucose monoesters and diesters and for example sucrose, glucose or methylglucose mono- or dioleates, stearates, behenates, oleopalmitates, linoleates, linolenates and oleostearates are used.

A non-limiting example that may be mentioned is the product sold under the name GLUCATE® DO by the company Amerchol, which is a methylglucose dioleate.

Non-limiting examples of esters or mixtures of esters of sugar and of fatty acid that may also be mentioned include:
  the products sold under the names F160, F140, F110, F90, F70 and SL40 by the company Crodesta, respectively corresponding to sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
  the products sold under the name RYOTO SUGAR ESTERS®, for example referenced B370 and corresponding to sucrose behenate formed from 20% monoester and 80% di-triester-polyester; and
  the sucrose mono-dipalmito-stearate sold by the company Goldschmidt under the name TEGOSOFT® PSE.

With regard to the cyclic ethers and cyclic esters, γ-butyrolactone, dimethyl isosorbide and diisopropyl isosorbide are non-limiting examples.

Silicone oils may also be used as an inert organic liquid phase.

Non-limiting examples of the silicone oils that are suitable are liquid, non-volatile silicone fluids with a viscosity of less than or equal to 10,000 mPa·s at 25° C., the viscosity of the silicones being measured according to ASTM standard 445 Appendix C.

Silicone oils are defined in greater detail in Walter Noll's "Chemistry and Technology of Silicones" (1968)—Academic Press.

Among the silicone oils that may be used according to the disclosure, non-limiting mention may be made of the silicone oils sold under the names DC-200 FLUID®-5 mPa·s, DC-200 FLUID®-20 mPa·s, DC-200 FLUID®E-350 mPa·s, DC-200 FLUID®-1000 mPa·s, DC-200 FLUID®-10 000 mPa·s DC-8566 AMINO FLUID® and DC 245 FLUID® by the company Dow Corning.

Mineral oils may also be used as an at least one inert organic liquid, for instance liquid paraffin, or petrolatum.

Plant oils may also be suitable, for example, but not limited to, avocado oil, olive oil, liquid jojoba wax and camellia oil, and also animal oils such as lanolin.

It is also possible to use apolar solvents, such as apolar dicapryl derivatives, for example dicapryl carbonate and dicapryl ether.

The at least one organic inert liquid is, in at least one embodiment, chosen from the polydecenes of formula $C_{10n}$ $H_{[(20n)+2]}$ wherein n is an integer ranging from 3 to 9, for example from 3 to 7, esters of fatty alcohols or of fatty acids, liquid petroleum jelly and liquid paraffin, and mixtures thereof.

In the compositions according to the disclosure, the at least one organic inert liquid is, in at least one aspect, present in a concentration ranging from 15% to 35%, for example from 18% to 30% by weight, relative to the total weight of the anhydrous composition.

The composition according to the disclosure may also comprise at least one nonionic amphiphilic polymer comprising at least one fatty chain.

Non-limiting examples of such polymers include:

(1) celluloses modified with groups comprising at least one fatty chain; non-limiting mention may be made, for example, of:

hydroxyethylcelluloses modified with groups comprising at least one fatty chain, such as alkyl, arylalkyl or alkylaryl groups, or mixtures thereof, and wherein the alkyl groups are, for example, $C_8$-$C_{22}$, such as the product NATROSOL PLUS GRADE® 330 CS ($C_{16}$ alkyls) sold by the company Aqualon, or the product BERMOCOLL EHM® 100 sold by the company Berol Nobel, and those modified with polyalkylene glycol alkylphenyl ether groups, such as the product AMERCELL POLYMER® HM-1500 (polyethylene glycol (15) nonylphenyl ether) sold by the company Amerchol.

(2) hydroxypropyl guars modified with groups comprising at least one $C_8$-$C_{22}$ fatty chain, such as the product JAGUAR® XC-95/3 ($C_{14}$ alkyl chain) sold by the company Rhodia, the product ESAFLOR® HM 22 ($C_{22}$ alkyl chain) sold by the company Lamberti, and the products RE210-18 ($C_{14}$ alkyl chain) and RE205-1 ($C_{20}$ alkyl chain) sold by the company Rhône-Poulenc.

(3) copolymers of vinylpyrrolidone and of hydrophobic monomers comprising a fatty chain;

non-limiting mention may be made, for example, of:

the products ANTARON® V216 or GANEX® V216 (vinylpyrrolidone/hexadecene copolymer) sold by the company I.S.P., and the products ANTARON® V220 or GANEX® V220 (vinylpyrrolidone/eicosene copolymer) sold by the company I.S.P.

(4) copolymers of $C_1$-$C_6$ alkyl acrylates or methacrylates and of amphiphilic monomers comprising at least one fatty chain.

(5) copolymers of hydrophilic acrylates or methacrylates and of hydrophobic monomers comprising at least one fatty chain, such as the polyethylene glycol methacrylate/lauryl methacrylate copolymer.

(6) polymers with an aminoplast ether skeleton comprising at least one fatty chain, such as the PURE THIX® compounds sold by the company Sud-Chemie.

(7) polyurethane polyethers comprising in their chain both hydrophilic blocks, for example of polyoxyethylenated nature, and hydrophobic blocks that may be aliphatic blocks alone and/or cycloaliphatic and/or aromatic blocks.

In at least one embodiment, the polyurethane polyethers comprise at least two hydrocarbon-based lipophilic chains, comprising from 6 to 30 carbon atoms, separated by a hydrophilic block, the hydrocarbon-based chains optionally being pendent chains or chains at the end of a hydrophilic block. According to one embodiment, it is possible for at least one pendent chain to be provided. In addition, the polymer may comprise a hydrocarbon-based chain at one or both ends of a hydrophilic block.

The polyurethane polyethers may be multiblock, for example, but not limited to, triblock form. The hydrophobic blocks may be at each end of the chain (for example, triblock copolymer comprising a hydrophilic central block) or distributed both at the ends and in the chain (for example, multiblock copolymer). These same polymers may also be graft polymers or starburst polymers.

In at least one aspect of the disclosure, the fatty-chain nonionic polyurethane polyethers may be triblock copolymers whose hydrophilic block is a polyoxyethylenated chain comprising from 50 to 1,000 oxyethylenated groups. The nonionic polyurethane polyethers comprise a urethane bond between the hydrophilic blocks.

By extension, also included among the fatty-chain nonionic polyurethane polyethers are those whose hydrophilic blocks are linked to the lipophilic blocks via other chemical bonds.

As examples of fatty-chain nonionic polyurethane polyethers that may be used in the disclosure, non-limiting mention may be made of SER-AD® FX 1100 from the company Servo Delden, which is a copolymer known under the European and US INCI name "STEARETH-100/PEG-136/HMDI Copolymer".

RHEOLATE® 205 comprising a urea function, sold by the company Rheox, or alternatively RHEOLATE® 208, 204 or 212 or ACRYSOL® RM 184, may also be used.

Non-limiting mention may also be made of the product ELFACOS® T210 comprising a $C_{12-14}$ alkyl chain and the product ELFACOS® T212 comprising a $C_{18}$ alkyl chain, from Akzo.

Non-limiting examples of the polyurethane polyethers that may be used according to the disclosure are those described in the article by G. Fonnum, J. Bakke and Fk. Hansen—Colloid Polym. Sci. 271, 380-389 (1993).

In at least one embodiment, the polyurethane polyethers comprise at least one $C_{10}$ to $C_{20}$ fatty chain, and the hydroxypropyl guars modified with groups comprise at least one $C_8$ to $C_{22}$ fatty chain.

The composition according to the disclosure may also comprise at least one anionic amphiphilic polymer comprising at least one fatty chain.

The at least one anionic amphiphilic polymer comprising at least one fatty chain that may be used according to the present disclosure are crosslinked or non-crosslinked polymers comprising:

hydrophilic units derived from at least one monomer comprising ethylenic unsaturation bearing a free carboxylic acid function, or a free or partially or totally neutralized sulfonic function, and hydrophobic units derived from at least one monomer comprising ethylenic unsaturation bearing a hydrophobic side chain, and optionally crosslinking units derived from at least one polyunsaturated monomers.

The at least one monomer comprising ethylenic unsaturation bearing a carboxylic acid function is chosen from ethacrylic acid, methacrylic acid, and acrylic acid, for example from methacrylic acid and acrylic acid and mixtures thereof.

The at least one monomer comprising ethylenic unsaturation bearing a hydrophobic side chain is chosen from (i) fatty alkyl esters of unsaturated carboxylic acids, and (ii) allyl fatty alkyl ethers.

(i) Non-limiting examples of the fatty alkyl esters of unsaturated carboxylic acids include those chosen from $C_{10-30}$, such as $C_{12-22}$, alkyl ethacrylates, methacrylates and/or acrylates. They encompass, for example, lauryl acrylate, stearyl acrylate, decyl acrylate, isodecyl acrylate and dodecyl acrylate, as well as the corresponding methacrylates, i.e. lauryl methacrylate, stearyl methacrylate, decyl methacrylate, isodecyl methacrylate and dodecyl methacrylate.

(ii) The allyl fatty alkyl ethers forming the hydrophobic units of the anionic amphiphilic polymers of the present disclosure correspond to the following formula (I):

$$CH_2=CR'CH_2OB_nR \quad (I)$$

wherein R' is chosen from a hydrogen atom and $CH_3$, B is an ethylenoxy group, n is an integer ranging from 0 to 100, R is a hydrocarbon-based group chosen from alkyl, arylalkyl, aryl, alkylaryl and cycloalkyl radicals comprising from 8 to 30 carbon atoms, for example from 10 to 24 carbon atoms such as from 12 to 18 carbon atoms. In at least one embodiment, R' is H, n is equal to 10, and R is a stearyl ($C_{18}$) radical.

Said crosslinking monomer is a compound comprising at least two non-conjugated polymerizable double bonds. Non-limiting examples include diallyl phthalate, allyl (meth)acrylate, divinylbenzene, (poly)ethylene glycol dimethacrylate, methylenebisacrylamide, polyallylsucrose or polyallylpentaerythritol.

Non-limiting examples of the anionic amphiphilic polymers of the type described above are described and prepared in U.S. Pat. Nos. 3,915,921 and 4,509,949 (copolymers of (meth)acrylic acid and of $C_{10-30}$ alkyl (meth)acrylates), and in patent EP-0 216 479 B2 (copolymers of (meth)acrylic acid and of allyl fatty alcohol ethers).

Non-limiting examples of polymers that may be mentioned are:

crosslinked polymers of acrylic acid and of $C_{10-30}$ alkyl methacrylate, such as CARBOPOL® ETD 2020 sold by the company Goodrich;

crosslinked polymers of acrylic acid and of $C_{10-30}$ alkyl acrylate, such as the polymers sold under the names CARBOPOL® 1382, PERMULEN® TR1 and PERMULEN® TR2 by the company Goodrich;

methacrylic acid/ethyl acrylate/oxyethylenated stearyl methacrylate (55/35/10) terpolymer;

(meth)acrylic acid/ethyl acrylate/25 EO oxyethylenated behenyl methacrylate terpolymer, and methacrylic acid/ethyl acrylate/steareth-10 allyl ether crosslinked terpolymer.

Non-limiting examples of the amphiphilic polymers comprising as hydrophilic units at least one ethylenically unsaturated monomer comprising a sulfonic group, in free or partially or totally neutralized form, and at least one hydrophobic portion, are described in French patent applications Nos. 0 016 954 and 0 100 328 by the Applicants, the content of which are incorporated by reference into the present disclosure.

Among these, non-limiting mention may be made of:

2-acrylamido-2-methylpropanesulfonic acid (AMPS)/n-dodecylacrylamide copolymer neutralized with sodium hydroxide, the copolymer crosslinked with methylenebisacrylamide comprising 75% by weight of AMPS units neutralized with $NH_3$ and of 25% by weight of acrylate units of GENAPOL® T-250, the copolymer crosslinked with allyl methacrylate comprising 90% by weight of AMPS units neutralized with $NH_3$ and of 10% by weight of methacrylate units of GENAPOL® T-250, or the crosslinked copolymer of allyl methacrylate comprising 80% by weight of AMPS units neutralized with $NH_3$ and of 20% by weight of methacrylate units of GENAPOL® T-250.

In the compositions according to the disclosure, the at least one nonionic amphiphilic polymer comprising at least one fatty chain and/or the at least one anionic amphiphilic polymer comprising at least one fatty chain may be present in a concentration ranging from 0.01% to 30% by weight, and for example from 0.01% to 15% by weight, relative to the total weight of the composition.

The compositions according to the disclosure may also comprise at least one water-soluble thickening polymer free of fatty chains.

The at least one water-soluble thickening polymer free of fatty chains that may be used in the compositions according to the disclosure include any water-soluble polymer that is synthetic or of natural origin conventionally used in cosmetics and other than the at least one nonionic amphilic polymer comprising at least one fatty chain and/or the at least one anionic amphiphilic polymer comprising at least one fatty chain as described above.

As examples of synthetic polymers, non-limiting mention may be made of polyvinylpyrrolidone, polyacrylic acid, polyacrylamide, non-crosslinked poly-2-acrylamidopropanesulfonic acid such as the product sold under the name SIMULGEL EG® by the company SEPPIC, crosslinked poly-2-acrylamido-2-methylpropanesulfonic acid, poly-2-acrylamido-2-methylpropanesulfonic acid crosslinked and partially neutralized with aqueous ammonia, sold under the brand name HOSTACORIN AMPS® by the company Clariant, mixtures with a synergistic thickening effect of the non-crosslinked poly-2-acrylamido-2-methylpropanesulfonic acid with hydroxyalkylcellulose ethers or with poly(ethylene oxide) as described in U.S. Pat. No. 4,540,510, or mixtures with a synergistic thickening effect of a poly(meth)acrylamido($C_1$-$C_4$)alkylsulfonic acid for example crosslinked with a crosslinked copolymer of maleic anhydride and of a ($C_1$-$C_5$)alkyl vinyl ether such as the mixture HOSTACORIN AMPS®/STABILEZE QM® (from the company ISF) and as described in French patent application No. 0 014 416 from the Applicants.

Non-limiting examples of the at least one water-soluble thickening polymer free of fatty chains of natural origin that may be used according to the present disclosure include polymers comprising at least one sugar unit, namely: nonionic guar gums; biopolysaccharide gums of microbial origin such as scleroglucan gum or xanthan gum; gums derived from plant exudates, such as gum arabic, ghatti gum, karaya gum, gum tragacanth, carrageenan, agar and carob gum; pectins; alginates; starches; hydroxy($C_1$-$C_6$)alkylcelluloses and carboxy($C_1$-$C_6$)alkylcelluloses.

For the purposes of the present disclosure, the expression "sugar unit" means a monosaccharide portion (monosaccharide or oside or simple sugar) or an oligosaccharide portion (short chains formed from the linking of monosaccharide units, which may be different) or a polysaccharide portion [long chains comprising monosaccharide units, which may be different, i.e. polyholosides or polyosides (homopolyosides or heteropolyosides)]. The saccharide units can also be substituted with alkyl, hydroxyalkyl, alkoxy, acyloxy or carboxyl groups, or alkyl radicals comprising from 1 to 4 carbon atoms.

The nonionic guar gums can be modified or unmodified.

The unmodified guar gums are, for example, but not limited to, the products sold under the name GUARGEL® D/15 by the company Goodrich, VIDOGUM® GH 175 by the company Unipectine and under the names MEYPROGUAR® 50 and JAGUAR® C by the company Meyhall.

The modified nonionic guar gums may be for example, but are not limited to, those modified with $C_1$-$C_6$ hydroxyalkyl groups.

Among the hydroxyalkyl groups that may be mentioned, non-limiting examples are hydroxymethyl, hydroxyethyl, hydroxypropyl and hydroxybutyl groups.

These guar gums are well known in the state of the art and can be prepared, for example, by reacting the corresponding alkene oxides such as propylene oxides, with the guar gum so as to obtain a guar gum modified with hydroxypropyl groups.

The degree of hydroxyalkylation, which corresponds to the number of alkylene oxide molecules consumed by the number of free hydroxyl functions present on the guar gum, for example, ranges from 0.4 to 1.2.

Such nonionic guar gums optionally modified with hydroxyalkyl groups are sold, for example, under the trade names JAGUAR® HP8, JAGUAR® HP60 and JAGUAR® HP120, JAGUAR® DC 293 and JAGUAR® HP 105 by the company Rhône-Poulenc (Meyhall) or under the name GALACTASOL® 4H4FD2 by the company Aqualon.

The biopolysaccharide gums of microbial origin, such as the scleroglucan or xanthan gums, the gums derived from plant exudates such as gum arabic, ghatti gum, karaya gum, gum tragacanth, carrageenan gum, agar gum and carob gum, the hydroxyalkylcelluloses and carboxymethylcelluloses, pectins, alginates and starches are well known to those skilled in the art and are described in, for example, but not limited to, the book by Robert L. Davidson entitled "Handbook of Water soluble gums and resins" published by McGraw Hill Book Company (1980).

Among these gums, the scleroglucans are represented by the products sold under the name ACTIGUM® CS by the company Sanofi Bio Industries, for example ACTIGUM® CS 11, and under the name AMIGEL® by the company Alban Muller International. Other scleroglucans, such as the one treated with glyoxal in French patent application No. 2 633 940, can also be used.

The xanthans include, as non-limiting examples, the products sold under the names KELTROL®, KELTROL® T, KELTROL® TF, KELTROL® BT, KELTROL® RD and KELTROL® CG by the company Nutrasweet Kelco, or under the names RHODICARE® S and RHODICARE® H by the company Rhodia Chimie.

Among the starch derivatives that may be mentioned, as a non-limiting example, is the product sold under the name PRIMOGEL® by the company Avebe.

The hydroxy($C_1$-$C_6$)alkylcelluloses include, for example, but not limited to, hydroxyethylcelluloses, such as those sold under the names CELLOSIZE® QP3L, CELLOSIZE® QP4400H, CELLOSIZE®QP30000H, CELLOSIZE® HEC30000A and CELLOSIZE® POLYMER PCG10 by the company Amerchol, or NATROSOL® 250HHR, NATROSOL® 250MR, NATROSOL® 250M, NATROSOL® 250HHXR, NATROSOL® 250HHX, NATROSOL® 250HR and NATROSOL® HX by the company Hercules, or TYLOSE® H1000 by the company Hoechst.

The hydroxy($C_1$-$C_6$)alkylcelluloses also include, but are not limited to, hydroxypropylcelluloses such as the products sold under the names KLUCEL® EF, KLUCEL® H, KLUCEL® LHF, KLUCEL® MF and KLUCEL® G by the company Aqualon.

In at least one embodiment, the carboxy($C_1$-$C_6$)alkylcelluloses used is carboxymethylcellulose, for which non-limiting mention may be made of the products sold under the names BLANOSE® 7M8/SF, BLANOSE RAFFINÉE® 7M, BLANOSE® 7LF, BLANOSE® 7MF, BLANOSE® 9M31F, BLANOSE® 12M31XP, BLANOSE® 12M31P, BLANOSE® 9M31XF, BLANOSE® 7H, BLANOSE® 7M31 and BLANOSE® 7H3SXF by the company Aqualon, or AQUASORB® A500 and AMBERGUM® 1221 by the company Hercules, or CELLOGEN® HP810A and CELLOGEN® HP6HS9 by the company Montello, or PRIMELLOSE® by the company Avebe.

When they are present in the pulverulent compositions of the present disclosure, the at least one water-soluble thickening polymer free of fatty chains is present in a weight proportion ranging from 0.01% to 30%, and for example from 0.01% to 15%, relative to the total weight of the composition.

The composition according to the disclosure may also comprise at least one hydrocarbon-based waxe, fluoro waxe or silicone waxe, or mixtures thereof. The silicone wax may be a wax comprising a silicone structure and units comprising at least one alkyl or alkoxy chain that are pendent and/or at the end of the silicone structure, these chains being linear or branched and comprising from 10 to 45 carbon atoms. These waxes are known, respectively, as alkyldimethicones and alkoxydimethicones. Moreover, these alkyl chains may comprise at least one ester function. As other waxes that may be used in the disclosure, non-limiting mention may be made of waxes of animal origin, for instance lanolins and beeswax; waxes of plant origin such as carnauba wax and candelilla wax; waxes of mineral origin, for instance paraffin wax, lignite wax and microcrystalline waxes, ceresin and ozokerite; synthetic waxes such as polyethylene waxes; and mixtures thereof.

In at least one embodiment, the composition according to the disclosure may comprise beeswax.

The composition according to the disclosure may also comprise other adjuvants, for example, but not limited to, fillers such as clays, binders such as vinylpyrrolidone, lubricants such as polyol stearates or alkali metal or alkaline-earth metal stearates, and also agents for controlling the release of oxygen such as magnesium carbonate or oxide, dyes or matting agents such as titanium oxides, or surfactants.

In at least one embodiment, the composition according to the disclosure comprises at least one surfactant chosen from anionic, nonionic, cationic, amphoteric, and zwitterionic surfactants.

Non-limiting examples of anionic surfactants that may be used, alone or as mixtures, in the context of the present disclosure, include salts (for example alkali metal salts, such as sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; ($C_6$-$C_{24}$) alkyl sulfosuccinates, ($C_6$-$C_{24}$) alkyl ether sulfosuccinates, ($C_6$-$C_{24}$) alkylamide sulfosuccinates; ($C_6$-$C_{24}$) alkyl sulfoacetates; ($C_6$-$C_{24}$) acyl sarcosinates, and ($C_6$-$C_{24}$) acyl glutamates. It is also possible to use ($C_6$-$C_{24}$) alkylpolyglycoside carboxylic esters such as alkylglucoside citrates, alkylpolyglycoside tartrates and alkylpolyglycoside sulfosuccinates, alkylsulfosuccinamates; acyl isethionates and N-acyl taurates, the alkyl or acyl radical of all of these different compounds, for example comprising from 12 to 20 carbon atoms, and the aryl radical, for example is chosen from phenyl and benzyl. Among the anionic surfactants that may also be used, non-limiting mention may also be made of fatty acid salts, such as oleic, ricinoleic, palmitic and stearic acid salts; coconut oil acid and hydrogenated coconut oil acid; and acyl lactylates wherein the acyl radical comprises from 8 to 20 carbon atoms. It is also possible to use alkyl D-galactoside uronic acids and their salts, polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example those comprising from 2 to 50 alkylene oxide groups, such as ethylene oxide groups, and mixtures thereof.

The nonionic surfactants are, themselves also, compounds that are well known (see for example "Handbook of Surfactants" by M. R. Porter, published by Blackie & Son (Glasgow and London), 1991, pp. 116-178). Thus, as non-limiting examples, they can be chosen from polyethoxylated, polypropoxylated, alkylphenols, alpha-diols and alcohols having a fatty chain comprising, for example, from 8 to 18 carbon atoms, it being possible for the number of ethylene oxide or propylene oxide groups to range, for example, from 2 to 50. Non-limiting mention may also be made of copolymers of ethylene oxide and of propylene oxide, condensates of ethylene oxide and of propylene oxide with fatty alcohols; polyethoxylated fatty amides for example having from 2 to 30 mol of ethylene oxide, polyglycerolated fatty amides comprising on average from 1 to 5, such as from 1.5 to 4, glycerol groups; polyethoxylated fatty amines, for example, comprising from 2 to 30 mol of ethylene oxide; oxyethylenated fatty acid esters of sorbitan comprising from 2 to 30 mol of ethylene oxide; fatty acid esters of sucrose, fatty acid esters of polyethylene glycol, alkylpolyglycosides, N-alkylglucamine derivatives, and amine oxides such as $(C_{10}\text{-}C_{14})$alkylamine oxides or N-acylaminopropylmorpholine oxides.

Non-limiting examples of the amphoteric or zwitterionic surfactants that may be used in the compositions according to the present disclosure can be, aliphatic secondary or tertiary amine derivatives wherein the aliphatic radical is a linear or branched chain comprising from 8 to 18 carbon atoms and comprising at least one water-solubilizing anionic group (for example carboxylate, sulfonate, sulfate, phosphate or phosphonate); non-limiting mention may also be made of $(C_8\text{-}C_{20})$alkylbetaines, sulfobetaines, $(C_8\text{-}C_{20})$alkylamido$(C_1\text{-}C_6)$alkylbetaines and $(C_8\text{-}C_{20})$alkylamido$(C_1\text{-}C_6)$alkylsulfobetaines.

Among the amine derivatives, non-limiting mention may be made of the products sold under the name MIRANOL®, as described in U.S. Pat. Nos. 2,528,378 and 2,781,354 and classified in the CTFA dictionary, 3rd edition, 1982, under the names Amphocarboxyglycinates and Amphocarboxypropionates, having the respective structures:

$$R_2\text{—CONHCH}_2\text{CH}_2\text{—N}(R_3)(R_4)(\text{CH}_2\text{COO}^-)$$

wherein: $R_2$ is chosen from an alkyl radical of an acid $R_2$—COOH present in hydrolysed coconut oil, heptyl, nonyl, and undecyl radicals, $R_3$ is a beta-hydroxyethyl group and $R_4$ is a carboxymethyl group; and $$R_{2'}\text{—CONHCH}_2\text{CH}_2\text{—N}(B)(C')$$

wherein:

B is —CH$_2$CH$_2$OX', C' is —(CH$_2$)$_z$—Y', wherein z is chosen from 1 and 2, X' is chosen from the —CH$_2$CH$_2$—COOH group and a hydrogen atom, Y' is chosen from —COOH and —CH$_2$—CHOH—SO$_3$H radicals, $R_{2'}$ is chosen from an alkyl radical of an acid $R_{2'}$—COOH present in coconut oil or in hydrolysed linseed oil, and an alkyl radical, for example a $C_7$, $C_9$, $C_{11}$ or $C_{13}$ alkyl radical, a $C_{17}$ alkyl radical and its iso-alkyl form, or an unsaturated $C_{17}$ radical.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphopropionate, Disodium Caprylamphodipropionate, Disodium Capryloamphodipropionate, Lauroamphodipropionic acid and Cocoamphodipropionic acid.

By way of example, non-limiting mention may be made of the cocoamphodiacetate sold under the trade name MIRANOL® C2M Concentrate by the company Rhodia Chimie.

Among the cationic surfactants that may be used in the composition according to the disclosure, non-limiting mention may be made of: salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; and amine oxides of cationic nature.

The composition according to the disclosure may also comprise at least one anhydrous cationic or amphoteric conditioning polymer, for instance those described in French patents 2 788 974 and 2 788 976 and as described below.

For the purposes of the present disclosure, the expression "cationic polymer" means any polymer comprising at least one cationic group and/or at least one group which may be ionized into a cationic group.

The cationic polymers which may be used in accordance with the present disclosure may be chosen from any of those already known as improving the cosmetic properties of the hair, for example, but not limited to, those described in patent application EP-A-337 354 and in French patents FR-2 270 846, 2 383 660, 2 598 611, 2 470 596 and 2 519 863.

In at least one embodiment, the cationic polymers are chosen from those comprising units comprised of primary, secondary, tertiary and/or quaternary amine groups, which may either form part of the main polymer chain or may be borne by a side substituent directly attached thereto.

The cationic polymers used can have a number-average molecular mass in a range from 500 to $5\times10^6$, for example from $10^3$ to $3\times10^6$.

Among the cationic polymers which may be mentioned, non-limiting examples include polymers of the polyamine, polyamino amide and polyquaternary ammonium type. These are known products. They are described, for example, in French patents Nos. 2 505 348 and 2 542 997. Among said polymers, non-limiting mention may be made of:

(1) Homopolymers or copolymers derived from acrylic or methacrylic esters or amides and comprising at least one of the units chosen from formula (II), (III), (IV), and (V) below:

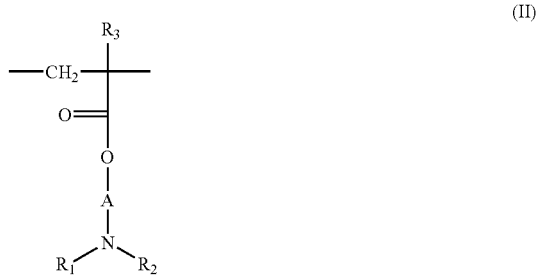

(II)

-continued

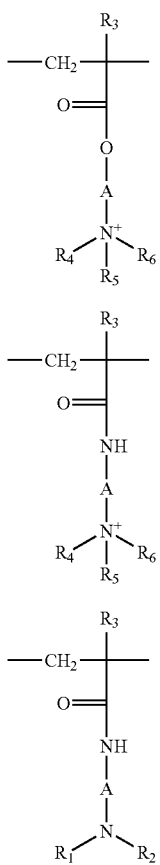

wherein:

$R_3$, which may be identical or different, is chosen from a hydrogen atom and a $CH_3$ radical;

A, which may be identical or different, is chosen from linear or branched alkyl groups comprising from 1 to 6 carbon atoms, for example from 2 to 3 carbon atoms, and hydroxyalkyl groups comprising from 1 to 4 carbon atoms;

$R_4$, $R_5$ and $R_6$, which may be identical or different, are chosen from alkyl groups comprising from 1 to 18 carbon atoms and a benzyl radical, and in at least one embodiment, the alkyl group comprises from 1 to 6 carbon atoms;

$R_1$ and $R_2$, which may be identical or different, are chosen from a hydrogen atom and alkyl groups comprising from 1 to 6 carbon atoms, for example methyl or ethyl;

X is an anion derived from an inorganic or organic acid, such as a methosulfate anion or a halide such as chloride or bromide.

The polymers of family (1) can also comprise at least one unit derived from comonomers which may be chosen from, but are not limited to, the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Thus, among these polymers of family (1), non-limiting mention may be made of:

copolymers of acrylamide and of dimethylaminoethyl methacrylate quaternized with dimethyl sulfate or with a dimethyl halide;

the copolymers of acrylamide and of methacryloyloxyethyltrimethylammonium chloride described, for example, in patent application EP-A-080 976;

the copolymer of acrylamide and of methacryloyloxyethyltrimethylammonium methosulfate;

quaternized or non-quaternized vinylpyrrolidone/dialkylaminoalkyl acrylate or methacrylate copolymers. These polymers are described in detail in French patents 2 077 143 and 2 393 573;

dimethylaminoethyl methacrylate/vinylcaprolactam/vinylpyrrolidone terpolymers;

vinylpyrrolidone/methacrylamidopropyldimethylamine copolymers; and quaternized vinylpyrrolidone/dimethylaminopropylmethacrylamide copolymers.

(2) The cellulose ether derivatives comprising quaternary ammonium groups, described in French patent 1 492 597. These polymers are also defined in the CTFA dictionary as quaternary ammoniums of hydroxyethylcellulose that has reacted with an epoxide substituted with a trimethylammonium group.

(3) Cationic cellulose derivatives such as cellulose copolymers or cellulose derivatives grafted with a water-soluble monomer of quaternary ammonium, and described for example in U.S. Pat. No. 4,131,576, such as hydroxyalkylcelluloses, for instance hydroxymethyl-, hydroxyethyl- or hydroxypropylcelluloses grafted, for example, with a methacryloylethyltrimethylammonium, methacrylamidopropyltrimethylammonium or dimethyldiallylammonium salt.

(4) The cationic polygalactomannans described, for example, in U.S. Pat. Nos. 3,589,578 and 4,031,307, such as guar gums comprising cationic trialkylammonium groups. Guar gums modified with a salt (e.g. chloride) of 2,3-epoxypropyltrimethylammonium are used, for example.

(5) Polymers comprising piperazinyl units and divalent alkylene or hydroxyalkylene radicals comprising straight or branched chains, optionally interrupted by oxygen, sulfur or nitrogen atoms or by aromatic or heterocyclic rings, as well as the oxidation and/or quaternization products of these polymers. Such polymers are described, for example, in French patents 2 162 025 and 2 280 361;

(6) Water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they comprise at least one tertiary amine function, they can be quaternized. Such polymers are described, for example, in French patents 2 252 840 and 2 368 508;

(7) The polyamino amide derivatives resulting from the condensation of polyalkylene polyamines with polycarboxylic acids followed by alkylation with difunctional agents. Non-limiting mention may be made, for example, of adipic acid/dialkylaminohydroxyalkyldialkylenetriamine polymers wherein the alkyl radical comprises from 1 to 4 carbon atoms and for example is chosen from methyl, ethyl, and propyl. Such polymers are described, for example, in French patent 1 583 363.

Among these derivatives, non-limiting mention may be made of the adipic acid/dimethylaminohydroxypropyl/diethylenetriamine polymers.

(8) The polymers obtained by reaction of a polyalkylene polyamine comprising two primary amine groups and at least one secondary amine group with a dicarboxylic acid chosen from diglycolic acid and saturated aliphatic dicarboxylic acids comprising from 3 to 8 carbon atoms. The molar ratio between the polyalkylene polyamine and the dicarboxylic acid is in a range from 0.8:1 to 1.4:1; the polyamino amide resulting therefrom is reacted with epichlorohydrin in a molar ratio of epichlorohydrin relative to the secondary amine group of the polyamino amide in a range from 0.5:1 to 1.8:1. Such polymers are described, for example, in U.S. Pat. Nos. 3,227,615 and 2,961,347.

(9) Cyclopolymers of alkyldiallylamine and of dialkyldiallylammonium, such as the homopolymers and copolymers comprising, as main constituent of the chain, units corresponding to formula (VI) or (VII):

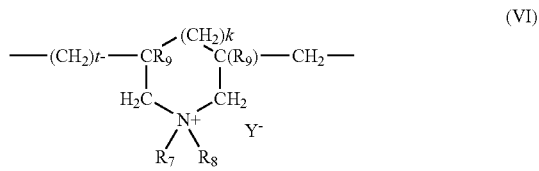

(VI)

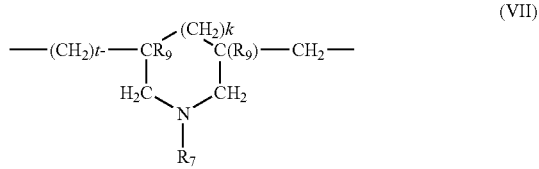

(VII)

wherein k and t are integers chosen from 0 and 1, the sum k+t being equal to 1; $R_9$ is chosen from a hydrogen atom and a methyl radical; $R_7$ and $R_8$, independently of each other, are chosen from alkyl groups comprising from 1 to 6 carbon atoms, hydroxyalkyl groups wherein the alkyl group, for example, comprises from 1 to 5 carbon atoms, and lower $C_1$-$C_4$ amidoalkyl groups, or $R_7$ and $R_8$ can, together with the nitrogen atom to which they are attached, be chosen from heterocyclic groups such as piperidyl or morpholinyl; $R_7$ and $R_8$, independently of each other, in at least one embodiment, are chosen from an alkyl group comprising from 1 to 4 carbon atoms; $Y^-$ is an anion, such as bromide, chloride, acetate, borate, citrate, tartrate, bisulfate, bisulfite, sulfate or phosphate. These polymers are described, for example, in French patent 2 080 759 and in its Certificate of Addition 2 190 406.

(10) The quaternary diammonium polymer comprising repeating units corresponding to the formula:

(VIII)

wherein:

$R_{10}$, $R_{11}$, $R_{12}$ and $R_{13}$, which may be identical or different, are chosen from aliphatic, alicyclic and arylaliphatic radicals comprising from 1 to 20 carbon atoms and lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally comprising a second heteroatom other than nitrogen, or alternatively $R_{10}$, $R_{11}$, $R_{12}$ and $R_{13}$ are chosen from a linear or branched $C_1$-$C_6$ alkyl radicals substituted with a nitrile, ester, acyl or amide group and groups —CO—O—$R_{14}$-D and —CO—NH—$R_{14}$-D wherein $R_{14}$ is an alkylene and D is a quaternary ammonium group;

$A_1$ and $B_1$ are chosen from polymethylene groups comprising from 2 to 20 carbon atoms which may be linear or branched, saturated or unsaturated, and which may comprise, linked to or intercalated in the main chain, at least one aromatic ring or at least one oxygen or sulfur atom or sulfoxide, sulfone, disulfide, amino, alkylamino, hydroxyl, quaternary ammonium, ureido, amide or ester group, $X^-$ is an anion derived from an inorganic or organic acid;

$A_1$, $R_{10}$ and $R_{12}$ can form, with the two nitrogen atoms to which they are attached, a piperazine ring; in addition, if $A_1$ is a linear or branched, saturated or unsaturated alkylene or hydroxyalkylene radical, $B_1$ can also be chosen from a group —($CH_2$)n-CO-D-OC—($CH_2$)n- wherein n is an integer ranging from 1 to 100 and for example from 1 to 50, and D is:

a) a glycol residue of formula: —O—Z—O—, wherein Z is chosen from linear or branched hydrocarbon-based radical and groups corresponding to one of the following formulae:

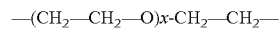

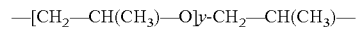

wherein x and y are integers ranging from 1 to 4, which is a defined and unique degree of polymerization or an average degree of polymerization;

b) a bis-secondary diamine residue, such as a piperazine derivative;

c) a bis-primary diamine residue of formula: —NH—Y—NH—, wherein Y is chosen from a linear or branched hydrocarbon-based radicals, and the divalent radical

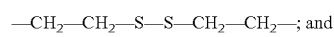

d) a ureylene group of formula: —NH—CO—NH—.

In at least one embodiment, $X^-$ is an anion, such as chloride or bromide.

These polymers may have a number-average molecular mass in a range from 1,000 to 100,000.

Non-limiting examples of polymers of this type are described in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is, for example, possible to use polymers that comprise repeating units corresponding to the following formula (IX):

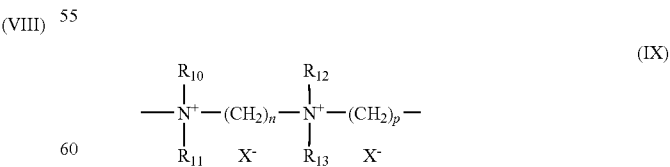

(IX)

wherein $R_{10}$, $R_{11}$, $R_{12}$ and $R_{13}$, which may be identical or different, are chosen from alkyl and hydroxyalkyl radicals comprising from 1 to 4 carbon atoms, n and p are independently chosen from integers ranging from 2 to 20, and $X^-$ is an anion derived from an inorganic or organic acid.

(11) Polyquaternary ammonium polymers comprising repeating units of formula (X):

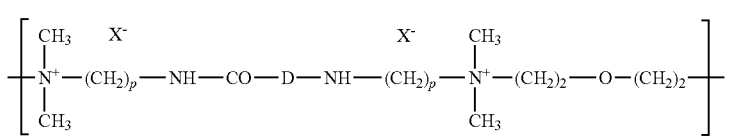

wherein p denotes an integer ranging from 1 to 6, D is chosen from a single bond and a group —$(CH_2)_r$—CO— wherein r is an integer chosen from 4 and 7, and $X^-$ is an anion;

Such polymers may be prepared according to the processes described in U.S. Pat. Nos. 4,157,388, 4,702,906 and 4,719,282. They are described, for example, in patent application EP-A-122 324.

(12) Quaternary polymers of vinylpyrrolidone and of vinylimidazole.

(13) Polyamines such as the product that is given under the reference name "Polyethylene glycol (15) Tallow polyamine" in the CTFA dictionary.

(14) Crosslinked methacryloyloxy($C_1$-$C_4$)alkyltri($C_1$-$C_4$) alkylammonium salt polymers, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound comprising olefinic unsaturation, for example methylenebisacrylamide. A crosslinked acrylamide/methacryloyloxyethyltrimethylammonium chloride copolymer (20/80 by weight) in the form of a dispersion comprising 50% by weight of said copolymer in mineral oil can be used, for example. This dispersion is sold under the name SALCARE® SC 92 by the company Allied Colloids. A crosslinked methacryloyloxyethyltrimethylammonium chloride homopolymer comprising 50% by weight of the homopolymer in mineral oil or in a liquid ester can also be used. These dispersions are sold under the names SALCARE® SC 95 and SALCARE® SC 96 by the company Allied Colloids.

Other cationic polymers which can be used in the context of the disclosure are polyalkyleneimines, for example polyethyleneimines, polymers comprising vinylpyridine or vinylpyridinium units, condensates of polyamines and of epichlorohydrin, quaternary polyureylenes and chitin derivatives.

The amphoteric polymers which may be used in accordance with the present disclosure may be chosen from polymers comprising units K and M randomly distributed in the polymer chain, wherein K is a unit derived from a monomer comprising at least one basic nitrogen atom and M is a unit derived from an acidic monomer comprising at least one carboxylic or sulfonic group, or alternatively K and M may be chosen from groups derived from zwitterionic carboxybetaine and sulfobetaine monomers;

K and M may also be a cationic polymer chain comprising primary, secondary, tertiary or quaternary amine groups, wherein at least one of the amine groups bears a carboxylic or sulfonic group linked via a hydrocarbon-based radical, or alternatively K and M form part of a chain of a polymer comprising an α,β-dicarboxylic ethylene unit wherein one of the carboxylic groups has been made to react with a polyamine comprising at least one primary or secondary amine group.

In at least one embodiment, the amphoteric polymers corresponding to the above definition are chosen from, but are not limited to, the following polymers:

(1) polymers resulting from the copolymerization of a monomer derived from a vinyl compound bearing a carboxylic group such as acrylic acid, methacrylic acid, maleic acid, α-chloroacrylic acid, and a basic monomer derived from a substituted vinyl compound comprising at least one basic atom, such as dialkylaminoalkyl methacrylate and acrylate, dialkylaminoalkylmethacrylamide and -acrylamide. Such compounds are described in U.S. Pat. No. 3,836,537. Non-limiting mention may also be made of the sodium acrylate/acrylamidopropyltrimethylammonium chloride copolymer.

The vinyl compound may also be a dialkyldiallylammonium salt such as dimethyldiallylammonium chloride.

(2) polymers comprising units derived from:

a) at least one monomer chosen from acrylamides and methacrylamides substituted on the nitrogen with an alkyl radical, b) at least one acidic comonomer comprising at least one reactive carboxylic group, and c) at least one basic comonomer, such as esters comprising primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides according to the disclosure, in at least one embodiment, are groups wherein the alkyl radicals comprises from 2 to 12 carbon atoms, for example N-ethylacrylamide, N-tert-butylacrylamide, N-tert-octylacrylamide, N-octylacrylamide, N-decylacrylamide, N-dodecylacrylamide and the corresponding methacrylamides.

In another aspect of the disclosure, the acidic comonomers may be chosen, for example, from acrylic acid, methacrylic acid, crotonic acid, itaconic acid, maleic acid and fumaric acid and alkyl monoesters, comprising from 1 to 4 carbon atoms, of maleic or fumaric acids or anhydrides.

In at least one embodiment, the basic comonomers are chosen from aminoethyl, butylaminoethyl, N,N'-dimethylaminoethyl, and N-tert-butylaminoethyl methacrylates.

(3) crosslinked and alkylated polyamino amides partially or totally derived from polyamino amides of general formula:

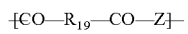  (XI)

wherein $R_{19}$ is chosen from divalent radicals derived from a saturated dicarboxylic acid, mono- or dicarboxylic aliphatic acids comprising an ethylenic double bond, esters of a lower alkanol, comprising from 1 to 6 carbon atoms, of these acids and radicals derived from the addition of any one of said acids to a bis(primary) or bis(secondary) amine, and Z is a bis (primary), mono- or bis(secondary) polyalkylene-polyamine radical and, in at least one embodiment, is chosen from:

a) in proportions ranging from 60 to 100 mol %, the radical

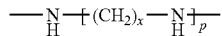
(XII)

wherein x is 2 and p is chosen from 2 and 3, or alternatively x is 3 and p is 2, this radical being derived from diethylenetriamine, from triethylenetetraamine or from dipropylenetriamine;

b) in proportions ranging from 0 to 40 mol %, the radical (XII) above wherein x is 2 and p is 1 and which is derived from ethylenediamine, or the radical derived from piperazine:

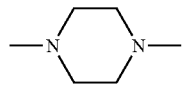

c) in proportions ranging from 0 to 20 mol %, the —NH—(CH$_2$)$_6$—NH— radical derived from hexamethylenediamine, these polyaminoamines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are, in at least one embodiment, chosen from acids comprising from 6 to 10 carbon atoms, such as adipic acid, 2,2,4-trimethyladipic acid and 2,4,4-trimethyladipic acid, terephthalic acid and acids comprising an ethylenic double bond such as, for example, acrylic acid, methacrylic acid and itaconic acid.

The alkane sultones used in the alkylation are, in at least one embodiment, propane sultone or butane sultone, and the salts of the alkylating agents are, for example, the sodium or potassium salts.

(4) polymers comprising zwitterionic units of formula:

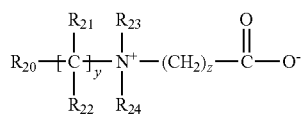
(XIII)

wherein R$_{20}$ is a polymerizable unsaturated group such as an acrylate, methacrylate, acrylamide or methacrylamide group, y and z are integers ranging from 1 to 3, R$_{21}$ and R$_{22}$, which may be identical or different, are chosen from a hydrogen atom, methyl, ethyl, and propyl, R$_{23}$ and R$_{24}$, which may be identical or different, are chosen from a hydrogen atom and an alkyl radical such that the sum of the carbon atoms in R$_{23}$ and R$_{24}$ does not exceed 10.

The polymers comprising such units can also comprise units derived from non-zwitterionic monomers such as dimethyl or diethylaminoethyl acrylate or methacrylate or alkyl acrylates or methacrylates, acrylamides or methacrylamides or vinyl acetate.

By way of example, non-limiting mention may be made of the copolymer of butyl methacrylate/dimethyl carboxymethylammonio ethyl methacrylate, such as the product sold under the name DIAFORMER® Z301 by the company Sandoz.

(5) polymers derived from chitosan comprising monomer units corresponding to formulae (XIV), (XV) and (XVI) below:

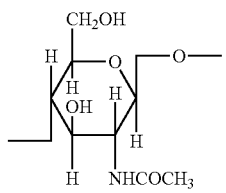
(XIV)

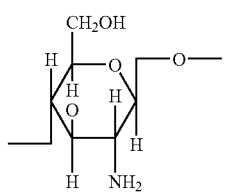
(XV)

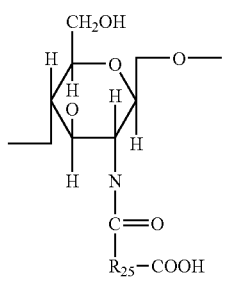
(XVI)

wherein the unit (XIV) is present in proportions ranging from 0 to 30%, the unit (XV) in proportions ranging from 5% to 50%, and the unit (XVI) in proportions ranging from 30% to 90%, it being understood that, in this unit (XVI), R$_{25}$ is a radical of formula:

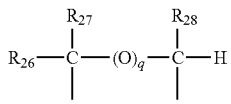

wherein q is an integer chosen from 0 and 1, if q is 0, R$_{26}$, R$_{27}$ and R$_{28}$, which may be identical or different, are chosen from a hydrogen atom, methyl, hydroxyl, acetoxy and amino residues, monoalkylamine residues and dialkylamine residues which are optionally interrupted by at least one nitrogen atom and/or optionally substituted with at least one amine, hydroxyl, carboxyl, alkylthio or sulfonic group, and alkylthio residues wherein the alkyl group bears an amino residue, wherein at least one of the radicals R$_{26}$, R$_{27}$ and R$_{28}$ is, in this case, a hydrogen atom;

or, if q is 1, R$_{26}$, R$_{27}$ and R$_{28}$ are each a hydrogen atom, as well as the salts formed by these compounds with bases or acids.

(6) polymers derived from the N-carboxyalkylation of chitosan, such as N-carboxymethylchitosan or N-carboxybutylchitosan.

(7) polymers corresponding to the general formula (XVII) as described, for example, in French patent 1 400 366:

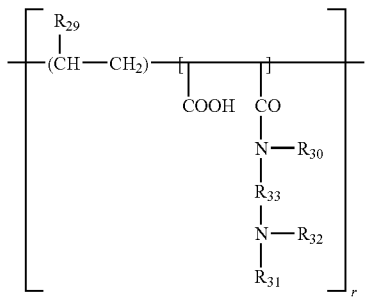

(XVII)

wherein $R_{29}$ is chosen from a hydrogen atom, $CH_3O$, $CH_3CH_2O$ and phenyl, $R_{30}$ is chosen from hydrogen and lower alkyl radicals, such as methyl or ethyl, $R_{31}$ is chosen from hydrogen and lower alkyl radicals, such as methyl or ethyl, $R_{32}$ is chosen from a lower alkyl radicals, such as methyl or ethyl, and radicals corresponding to the formula: —$R_{33}$—$N(R_{31})_2$, wherein $R_{33}$ and $R_{31}$ are as defined herein, $R_{33}$ is chosen from —$CH_2$—$CH_2$—, —$CH_2$—$CH_2$—$CH_2$— and —$CH_2$—$CH(CH_3)$—, as well as the higher homologues of these radicals and comprising up to 6 carbon atoms, r is an integer such that the molecular weight of the final polymer is in a range from 500 to 6,000,000, for example from 1,000 to 1,000,000.

(8) amphoteric polymers of the type -D-X-D-X— chosen from:

a) polymers obtained by the action of chloroacetic acid or sodium chloroacetate on compounds comprising at least one unit of formula:

-D-X-D-X-D-            (XVIII)

wherein D is a radical

and X is chosen from E and E', wherein E or E', which may be identical or different, are divalent radicals which are alkylene radicals with a straight or branched chain comprising up to 7 carbon atoms in the main chain, which is unsubstituted or substituted with hydroxyl groups and which can comprise, in addition to the oxygen, nitrogen and sulfur atoms, from 1 to 3 aromatic and/or heterocyclic rings; wherein the oxygen, nitrogen and sulfur atoms are present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) polymers of formula:

-D-X-D-X—            (XIX)

wherein D is a radical

and X is chosen from E and E' and at least once E'; wherein E has the meaning given above and E' is a divalent radical which is an alkylene radical with a straight or branched chain comprising up to 7 carbon atoms in the main chain, which is unsubstituted or substituted with at least one hydroxyl radical and comprises at least one nitrogen atom, wherein the nitrogen atom is substituted with an alkyl chain which is optionally interrupted by an oxygen atom and necessarily comprises at least one carboxyl function or at least one hydroxyl function and is betainized by reaction with chloroacetic acid or sodium chloroacetate.

(9) ($C_1$-$C_5$)alkyl vinyl ether/maleic anhydride copolymers partially modified by semiamidation with an N,N-dialkylaminoalkylamine, such as N,N-dimethylaminopropylamine, or by semiesterification with an N,N-dialkanolamine. These copolymers can also comprise other vinyl comonomers such as vinylcaprolactam.

In at least one embodiment, the cationic or amphoteric polymers that may be used according to the present disclosure are chosen from, but are not limited to:

(i) among the cationic polymers:

the dimethyldiallylammonium chloride homopolymer sold under the name MERQUAT® 100Dry by the company Calgon;

the copolymers of dimethyldiallylammonium chloride and of acrylamide that are sold under the name MERQUAT® 2200 by the company Calgon;

the polymers of poly(quaternary ammonium) type prepared and described in French patent 2 270 846, comprising repeating units of formulae (W) and (U) below:

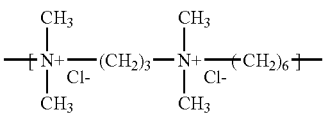

(W)

and for example those whose weight-average molar mass, determined by gel permeation chromatography, is in a range from 9,500 to 9,900;

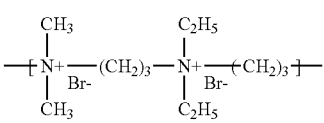

(U)

and for example those whose weight-average molar mass, determined by gel permeation chromatography, is 1,200; and polymers of poly(quaternary ammonium) type of family (11) and of formula (X) wherein $X^-$ is chlorine, and for example those whose weight-average molecular mass is less than 100,000 such as less than or equal to 50,000;

(ii) among the amphoteric polymers:
the dimethyldiallylammonium chloride/acrylic acid (80/20) copolymer sold under the name MERQUAT® 280 Dry by the company Calgon (CTFA name: Polyquaternium 22);
the dimethyldiallylammonium chloride/acrylic acid (95/5) copolymer sold under the name MERQUAT® 295 Dry by the company Calgon (CTFA name: Polyquaternium 22);
the copolymer of methacrylamidopropyltrimonium chloride, of acrylic acid and of ethyl acrylate, sold under the name MERQUAT® 2001 by the company Calgon (CTFA name: Polyquaternium 47); and
the acrylamide/dimethyldiallylammonium chloride/acrylic acid terpolymer sold under the name MERQUAT PLUS® 3330 Dry by the company Calgon (CTFA name: Polyquaternium 39).

When they are present in the pulverulent compositions of the present disclosure, the cationic and/or amphoteric polymers are present in a weight proportion of less than or equal to 20% relative to the total weight of the said composition and for example less than or equal to 8%.

In at least one embodiment, the anhydrous composition in paste form is constituted by mixing at least one powder and at least one inert liquid.

The anhydrous composition according to the disclosure may be prepared by dispersing, under mechanical action, all the pulverulent compounds in the inert organic liquid, in which the other liquid compounds of the composition have been predispersed or premixed.

The composition may also be prepared by extrusion, by introducing the liquid and solid phases of the composition into the extruder, and then mixing them at a temperature below 25° C. using a co-rotating twin-screw system composed of transportation and blending components.

The anhydrous composition according to the disclosure may be used for the preparation of a ready-to-use composition that results from the extemporaneous mixing of the anhydrous composition with an aqueous composition optionally comprising hydrogen peroxide.

This mixing is, in at least one embodiment, performed immediately before applying the product to the hair.

According to one embodiment, the ready-to-use composition results from the extemporaneous mixing of the anhydrous composition with an aqueous composition not comprising hydrogen peroxide.

The anhydrous composition in paste form according to the disclosure can be mixed with 0.5 to 10 weight equivalents of an aqueous composition, which may be a solution, an emulsion or a gel.

When the aqueous composition comprises hydrogen peroxide, it has a weight concentration of hydrogen peroxide ranging from 2% to 12%, for example from 2% to 6%. It may also comprise hydrogen peroxide stabilizers such as sodium pyrophosphate, sodium stannate and sodium salicylate.

When the aqueous composition comprises hydrogen peroxide, it may, for example, have a pH of less than 7. An acidic pH promotes the stability of the hydrogen peroxide in the composition. It may be obtained by means of acidifying agents, non-limiting examples of which include hydrochloric acid, acetic acid, etidronic acid, phosphoric acid, lactic acid and boric acid, and may be conventionally adjusted by adding either basifying agents, for instance aqueous ammonia, monoethanolamine, diethanolamine, triethanolamine, isopropanolamine, 1,3-diaminopropane, alkali metal and ammonium (bi)carbonate, organic carbonates, such as guanidine carbonate, or alkaline hydroxides, it being possible for all these compounds to be taken alone or as a mixture.

Whether or not it comprises hydrogen peroxide, the aqueous composition may also comprise preserving agents, colorants, fragrances, antifoams, and also sequestering agents, for instance ethylenediaminetetraacetic acid (EDTA) or pentasodium pentetate (CTFA name).

Needless to say, a person skilled in the art will take care to select the optional additional compound or compounds mentioned above, such that the properties intrinsically associated with the anhydrous composition in paste form or with the ready-to-use bleaching composition according to the disclosure are not, or are not substantially, adversely affected by the envisaged addition or additions.

The pH of the ready-to-use bleaching composition can be in a range from 7 to 12. In at least one embodiment, it is in a range from 7.5 to 11.

In at least one aspect of the disclosure, the bleaching process according to the disclosure comprises mixing, immediately before use, an anhydrous composition as described above with an anhydrous composition as described above, optionally comprising hydrogen peroxide, applying the ready-to-use bleaching composition thus obtained to the area of (wet or dry) human keratin fibers to be bleached and leaving the composition to act for a leave-on time that is sufficient to obtain the desired bleaching, for example ranging from 1 to 60 minutes, such as from 10 to 45 minutes, and removing the bleaching mixture by rinsing with water, followed by washing with a shampoo, and then optionally drying.

According to another aspect, the aqueous composition is water.

Another aspect of the present disclosure is a multi-compartment device, or "kit", for bleaching human keratin fibers such as the hair, characterized in that it comprises at least two compartments, one of which comprises an anhydrous composition as described above, and the other comprises an aqueous composition as described above, optionally comprising hydrogen peroxide.

A further aspect of the present disclosure is the use of an anhydrous composition as described above for the preparation of a ready-to-use keratin fiber bleaching composition, by mixing with an aqueous composition optionally comprising hydrogen peroxide.

In at least one aspect, in the use of an anhydrous composition as described above for the preparation of a ready-to-use keratin fiber bleaching composition, no aqueous hydrogen peroxide composition is employed. In a further embodiment, the preparation is prepared by mixing the anhydrous composition according to the disclosure with an aqueous composition not comprising hydrogen peroxide.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

The examples that follow are given as illustrations of the present disclosure, and should not be taken as limiting its scope.

EXAMPLES

In the examples that follow, all the amounts are indicated as weight percentages of active material relative to the total weight of the composition, unless otherwise indicated.

Two compositions were prepared from the ingredients indicated in the table below.

Example 1

Composition B according to the disclosure comprises 10% by weight of a complex of polyvinylpyrrolidone (PVP) and of hydrogen peroxide ($H_2O_2$), whereas comparative composition A is a standard composition not comprising such a complex.

| Ingredients (weight % AM) | Composition A comparative | Composition B according to the disclosure |
|---|---|---|
| Potassium persulfate | 34.75 | 34.75 |
| Sodium persulfate | 6 | 6 |
| Sodium metasilicate | 3.4 | 3.4 |
| Sodium disilicate | 14.2 | 14.2 |
| Ammonium chloride | 4.2 | 4.2 |
| EDTA | 0.2 | 0.2 |
| Titanium dioxide | 1 | 0 |
| Sodium lauryl sulfate (EMPICOL ® LX/N from Huntsman) | 4 | 1 |
| Magnesium stearate | 2 | 0 |
| Polyurethane (RHEOLATE ® FX11000 from Elementis) | 2 | 0 |
| Carboxymethyl starch (PRIMOJEL ® from DMV International) | 2 | 0 |
| Colloidal silica (LEVILITE ® Standard from CECA) | 1 | 0 |
| PVP-$H_2O_2$ complex (PEROXYDONE ® K-30 from ISP) | 0 | 10 |
| Mineral oil (MARCOL ® 82 from Exxon-Mobil) | 1 | 1 |
| Xanthan gum (KELTROL ® CGBT from CP Kelco) | 1.4 | 2.4 |
| Beeswax | 1.2 | 1.2 |
| Isopropyl myristate | 21.6 | 21.6 |
| Ceramide (MEXANYL ® GZ from Chimex) | 0.01 | 0.01 |
| Ultramarine blue 09 | 0.04 | 0.04 |

AM = active material

Compositions A and B were mixed in a ratio 1:1.5 by weight with an aqueous hydrogen peroxide composition at 12% by weight, and the ready-to-use compositions thus formed were applied to locks of chestnut-brown hair with a bath ratio of 10, for a leave-on time of 40 minutes, at a temperature of 27° C. After treatment, the locks were then rinsed with water, shampooed and then dried.

Applicants performed colorimetric measurements on the locks of bleached hair thus obtained.

The bleaching power of compositions A and B was measured using a MINOLTA® CM 2002 calorimeter in the international CIE L*a*b* system.

The values obtained are as follows:

|  | L* | a* | b* |
|---|---|---|---|
| Composition A | 49.2 | 12.1 | 29 |
| Composition B | 53.3 | 11.5 | 30.4 |

In these values, L* represents the lightness of the shade obtained. The value L* is in a range from 0 to 100. The higher this value, the lighter the shade.

The lock obtained using composition B was lighter than that obtained using composition A.

These results show that the lightening or bleaching performance qualities obtained with the composition of the disclosure are superior to those of the prior art.

Example 2

| Ingredients (weight % AM) | Composition C according to the disclosure |
|---|---|
| Potassium persulfate | 33 |
| Sodium persulfate | 6 |
| Sodium metasilicate | 3.4 |
| Sodium disilicate | 12 |
| Ammonium chloride | 4.2 |
| EDTA | 0.2 |
| Sodium lauryl sulfate (EMPICOL ® LX/N from Huntsman) | 1 |
| PVP-$H_2O_2$ complex (PEROXYDONE ® K-30 from ISP) | 20 |
| Mineral oil (MARCOL ® 82 from Exxon-Mobil) | 17 |
| Xanthan gum (KELTROL ® CGBT from CP Kelco) | 2 |
| Beeswax | 1.2 |

AM = active material

Composition C was mixed in a ratio 1:1.5 by weight with water and the ready-to-use composition thus formed was then applied to locks of chestnut-brown hair with a bath ratio of 10, for a leave-on time of 40 minutes, at a temperature of 27° C. A good lightening effect was obtained.

What is claimed is:

1. An anhydrous composition in paste form for bleaching keratin fibers, comprising at least one peroxygenated salt, at least one alkaline agent, and at least one complex of hydrogen peroxide and of at least one polymer comprising, as a monomer, at least one vinyl heterocyclic monomer.

2. The composition according to claim 1, wherein the at least one vinyl heterocyclic monomer is chosen from monomers comprising an optionally substituted 4- to 6-membered heterocycle optionally fused to a benzene ring, comprising from 1 to 4 identical or different endocyclic heteroatoms; wherein the number of endocyclic heteroatoms is less than that of the ring members of the heterocycle; and wherein the heteroatom or heteroatoms are chosen from sulfur, oxygen, and nitrogen atoms.

3. The composition according to claim 1, wherein the at least one vinyl heterocyclic monomer is chosen from N-vinyl monomers.

4. The composition according to claim 3, wherein the at least one vinyl heterocyclic monomer is chosen from N-vinylpyrrolidone, vinylcaprolactam, N-vinylpiperidone, N-vinyl-3-morpholine, N-vinyl-4-oxazolinone, 2-vinylpyridine, 4-vinylpyridine, 2-vinylquinoline, 1-vinylimidazole and 1-vinylcarbazole, which are optionally substituted.

5. The composition according to claim 4, wherein the at least one vinyl heterocyclic monomer is vinylpyrrolidone.

6. The composition according to claim 1, wherein the at least one polymer further comprises, at least one other monomer chosen from vinyl acetate, (meth)acrylic acids, (meth)acrylamides, $C_1$-$C_4$ alkyl esters of (meth)acrylic acid, and substituted or unsubstituted $C_1$-$C_4$ alkyl esters of (meth) acrylic acid.

7. The composition according to claim 1, wherein the at least one polymer comprising, as a monomer, at least one vinyl heterocyclic monomer is a homopolymer.

8. The composition according to claim 1, wherein the at least one complex of hydrogen peroxide and of at least one polymer comprises from 10% to 30% by weight of hydrogen peroxide, relative to the total weight of the complex.

9. The composition according to claim 1, wherein, in the at least one complex of hydrogen peroxide and of at least one polymer comprising, as a monomer, at least one vinyl heterocyclic monomer, the mole ratio between the at least one vinyl heterocyclic monomer and the hydrogen peroxide ranges from 0.5 to 2.

10. The composition according to claim 1, wherein the composition comprises from 0.1% to 50% by weight of the at least one complex of hydrogen peroxide and of at least one polymer, relative to the total weight of the composition.

11. The composition according to claim 1, wherein the at least one peroxygenated salt is chosen from ammonium persulfates, alkali metal persulfates, ammonium perborates, alkali metal perborates, ammonium percarbonates, alkali metal percarbonates, magnesium peroxide, and mixtures of these compounds.

12. The composition according to claim 1, wherein the at least one peroxygenated salt is present in a concentration ranging from 10% to 70% by weight, relative to the total weight of the composition.

13. The composition according to claim 1, wherein the at least one alkaline agent is chosen from aqueous ammonia, and alkali metal and alkaline-earth metal salts of silicates, metasilicates, phosphates, hydrogen phosphates, carbonates, and hydrogen carbonates.

14. The composition according to claim 1, wherein the at least one alkaline agent is present in a concentration ranging from 0.01% to 40% by weight, relative to the total weight of the composition.

15. The composition according to claim 1, wherein the composition further comprises at least one ammonium salt.

16. The composition according to claim 15, wherein the at least one ammonium salt is present in a concentration ranging from 0.01% to 40% by weight, relative to the total weight of the composition.

17. The composition according to claim 16, wherein the at least one ammonium salt is present in a concentration ranging from 0.1% to 30% by weight, relative to the total weight of the composition.

18. The composition according to claim 1, wherein the composition further comprises at least one inert organic liquid.

19. The composition according to claim 18, wherein the at least one inert organic liquid is chosen from polydecenes of formula $C_{10n}H_{[(20n)+2]}$ wherein n is in a range from 3 to 9, esters of fatty alcohols, esters of fatty acids, esters of sugars, diesters of sugars, esters of $C_{12}$-$C_{24}$ fatty acids, diesters of $C_{12}$-$C_{24}$ fatty acids, cyclic ethers, cyclic esters, silicone oils, mineral oils, plant oils, and mixtures thereof.

20. The composition according to claim 19, wherein the at least one inert organic liquid is chosen from polydecenes, esters of fatty alcohols, esters of fatty acids, mineral oils, and mixtures thereof.

21. The composition according to claim 18, wherein the at least one inert organic liquid is present in a concentration ranging from 15% to 35% by weight, relative to the total weight of the composition.

22. The composition according to claim 21, wherein the at least one inert organic liquid is present in a concentration ranging from 18% to 30% by weight, relative to the total weight of the composition.

23. The composition according to claim 1, wherein the composition further comprises at least one nonionic amphiphilic polymer comprising at least one fatty chain.

24. The composition according to claim 1, wherein the composition further comprises at least one anionic amphiphilic polymer comprising at least one fatty chain.

25. The composition according to claim 1, wherein the composition further comprises at least one water-soluble thickening polymer free of fatty chains.

26. The composition according to claim 1, wherein the composition further comprises at least one surfactant chosen from anionic, nonionic, cationic, amphoteric, and zwitterionic surfactants.

27. The composition according to claim 1, wherein the composition further comprises at least one anhydrous cationic or amphoteric conditioning polymer.

28. A ready-to-use composition resulting from the extemporaneous mixing of an anhydrous composition comprising at least one peroxygenated salt, at least one alkaline agent, and at least one complex of hydrogen peroxide and of at least one polymer comprising, as a monomer, at least one vinyl heterocyclic monomer, with an aqueous composition optionally comprising hydrogen peroxide.

29. The composition according to claim 28, wherein the aqueous composition does not comprise hydrogen peroxide.

30. A process for bleaching human keratin fibers, comprising mixing, immediately before use, an anhydrous composition comprising at least one peroxygenated salt, at least one alkaline agent, and at least one complex of hydrogen peroxide and of at least one polymer comprising, as a monomer, at least one vinyl heterocyclic monomer, with an aqueous composition optionally comprising hydrogen peroxide, applying the composition thus obtained to the area of the human keratin fibers to be bleached, leaving it to act for a leave-on time that is sufficient to obtain the desired bleaching, removing the bleaching mixture by rinsing with water, optionally followed by washing with a shampoo, and then optionally drying.

31. A process according to claim 30, wherein the aqueous composition is water.

32. A multi-compartment device for bleaching human keratin fibers comprising at least two compartments, wherein one compartment comprises an anhydrous composition comprising at least one peroxygenated salt, at least one alkaline agent, and at least one complex of hydrogen peroxide and of at least one polymer comprising, as a monomer, at least one vinyl heterocyclic monomer, and a second compartment comprising an aqueous composition optionally comprising hydrogen peroxide.

33. A method for the preparation of a ready-to-use keratin fiber bleaching composition comprising mixing an anhydrous composition comprising at least one peroxygenated salt, at least one alkaline agent, and at least one complex of hydrogen peroxide and of at least one polymer comprising, as a monomer, at least one vinyl heterocyclic monomer, with an aqueous composition optionally comprising hydrogen peroxide.

34. A method according to claim 33, wherein the aqueous composition does not comprise hydrogen peroxide.

* * * * *